(12) United States Patent
Bernard et al.

(10) Patent No.: US 10,463,333 B2
(45) Date of Patent: Nov. 5, 2019

(54) SYNTHETIC IMAGES FOR BIOPSY CONTROL

(71) Applicant: General Electric Company, Schenectady, NY (US)

(72) Inventors: Sylvain Bernard, Buc (FR); Giovanni Palma, Buc (FR)

(73) Assignee: General Electric Company, Schenectady, NY (US)

( * ) Notice: Subject to any disclaimer, the term of this patent is extended or adjusted under 35 U.S.C. 154(b) by 227 days.

(21) Appl. No.: 15/377,465

(22) Filed: Dec. 13, 2016

(65) Prior Publication Data

US 2018/0165840 A1 Jun. 14, 2018

(51) Int. Cl.
| | |
|---|---|
| G06K 9/00 | (2006.01) |
| A61B 6/00 | (2006.01) |
| A61B 6/02 | (2006.01) |
| A61B 6/12 | (2006.01) |
| A61B 34/30 | (2016.01) |
| A61B 34/10 | (2016.01) |

(Continued)

(52) U.S. Cl.
CPC ............ *A61B 6/502* (2013.01); *A61B 6/022* (2013.01); *A61B 6/025* (2013.01); *A61B 6/12* (2013.01); *A61B 6/463* (2013.01); *A61B 6/5205* (2013.01); *A61B 6/5235* (2013.01); *A61B 6/5247* (2013.01); *A61B 34/10* (2016.02); *A61B 34/30* (2016.02); *G06T 11/008* (2013.01); *A61B 5/055* (2013.01); *A61B 6/0414* (2013.01); *A61B 6/5252* (2013.01); *A61B 6/5258* (2013.01); *A61B 8/0825* (2013.01); *A61B 10/0233* (2013.01); *A61B 2010/045* (2013.01); *A61B 2017/3405* (2013.01); *A61B 2034/107* (2016.02); *A61B 2090/367* (2016.02)

(58) Field of Classification Search
CPC ....... G06T 11/003; A61B 6/463; A61B 6/022; A61B 6/025; A61B 6/502; A61B 90/11; A61B 6/5247
USPC ........................................................ 382/131
See application file for complete search history.

(56) References Cited

U.S. PATENT DOCUMENTS

| | | |
|---|---|---|
| 7,881,428 B2 | 2/2011 | Jing et al. |
| 8,452,379 B2 | 5/2013 | Defreitas et al. |
| (Continued) | | |

FOREIGN PATENT DOCUMENTS

| | | |
|---|---|---|
| EP | 1351192 A1 | 10/2003 |
| EP | 1792569 A2 | 6/2007 |
| (Continued) | | |

OTHER PUBLICATIONS

Kalke et al., "Sinogram Interpolation Method for Sparse-Angle Tomography", Applied Mathematics, Feb. 2014, vol. 5, pp. 423-441.
GE Healthcare Brochure—SenoClaire 3D Breast Tomosynthesis, 2014.

*Primary Examiner* — Van D Huynh
(74) *Attorney, Agent, or Firm* — Andrus Intellectual Property Law, LLP

(57) ABSTRACT

Abstract systems and methods of biopsy control include reconstructing a 3D volume from a plurality of tomosynthesis projection images and producing a plurality of synthetic stereo images from the plurality of tomosynthesis projection images. At least the synthetic stereo images are presented on a graphical display to a clinician to facilitate at least one input of a biopsy location for biopsy control.

25 Claims, 7 Drawing Sheets

(51) Int. Cl.
*G06T 11/00* (2006.01)
*A61B 5/055* (2006.01)
*A61B 8/08* (2006.01)
*A61B 6/04* (2006.01)
*A61B 10/04* (2006.01)
*A61B 90/00* (2016.01)
*A61B 17/34* (2006.01)
*A61B 10/02* (2006.01)

(56) References Cited

U.S. PATENT DOCUMENTS

| | | | |
|---|---|---|---|
| 8,565,374 | B2 | 10/2013 | Defreitas et al. |
| 8,824,761 | B2 | 9/2014 | Palma et al. |
| 2007/0225600 | A1* | 9/2007 | Weibrecht ............... A61B 6/025 600/429 |
| 2007/0268999 | A1* | 11/2007 | Ullberg ................. A61B 6/025 378/21 |
| 2008/0045833 | A1* | 2/2008 | Defreitas ............... A61B 6/025 600/429 |
| 2008/0187095 | A1* | 8/2008 | Boone .................. A61B 6/0435 378/37 |
| 2011/0150178 | A1 | 6/2011 | Bernard et al. |
| 2012/0121064 | A1 | 5/2012 | Bernard |
| 2013/0090553 | A1* | 4/2013 | Maack ................... A61B 6/022 600/424 |
| 2016/0042537 | A1* | 2/2016 | Ng ........................ G06T 11/005 382/131 |
| 2016/0089098 | A1* | 3/2016 | Nakayama ............. A61B 6/502 600/424 |
| 2016/0235380 | A1* | 8/2016 | Smith ................... A61B 6/025 |

FOREIGN PATENT DOCUMENTS

| | | |
|---|---|---|
| FR | 2905256 A | 3/2008 |
| GB | 2533801 A | 7/2016 |
| JP | 2015506794 A1 | 3/2015 |
| WO | 01/80184 | 10/2001 |

* cited by examiner

SYNTHETIC IMAGES FOR BIOPSY CONTROL

BACKGROUND

The present disclosure relates to the field of image processing. More specifically, the present disclosure is related to the field of image processing to create synthetic images from tomographic projection images for use in controlling a needle biopsy.

Mammography imaging is commonly used in the screening and detection of breast cancer. Specifically, mammography imaging is used to detect lesions within the breast. Frequently, a combination of full field digital mammography (FFDM) and/or digital breast tomography (DBT) is used to detect lesions and/or calcifications within the breast. A two dimensional (2D) FFDM image shows a projection of the tissue matrix, e.g. a breast for breast cancer diagnosis, onto a plane formed by a detector, from a radiation source. However, an FFDM image is a two dimensional projection of a three dimensional (3D) tissue matrix. Tissue super position may mask lesions sought to be biopsied and the true position of a lesion or a biopsy needle within the tissue matrix may be obscured. DBT imaging acquires a plurality of projection images and allows a 3D representation of the tissue matrix to be obtained in the form of a series of successive slices. While the slices of the 3D reconstruction can provide relative information regarding the position of a lesion or instrument, the exact position of the object within the thickness of the slice may be obscured as in FFDM images. Furthermore, if the lesion or instrument is located across two or more tomographic slices, the relative position, size, and volume of such object may be difficult to determine.

Therefore, currently available FFDM and DBT imaging solutions have limitations when a clinician tries to determine and/or identify a center of a lesion to be biopsied, for example in the control of a robotic or automated needle biopsy. Improved accuracy in identifying instrument position and/or the target location for biopsy (e.g. the center of a lesion) improves the accuracy of obtaining a desired biopsy sample, and reduces the chance of missing the lesion or obtaining an incomplete biopsy sample, either of which would result in an increased number of samples to be acquired during the biopsy procedure, thereby resulting in increased pain and/or discomfort to the patient.

BRIEF DISCLOSURE

An exemplary embodiment of a method of generating images for biopsy control includes receiving a plurality of tomographic projection images. A three dimensional (3D) volume is reconstructed from the plurality of tomographic projection images. A plurality of synthetic full field digital mammography (FFDM) images are produced from the plurality of tomographic projection images. The synthetic stereo images are presented on a graphical display to a clinician for receiving at least one input for biopsy control.

An exemplary embodiment of a system for biopsy control includes an acquisition unit. The acquisition unit includes a radiation source and an X-ray detector. The radiation source is moveable relative to the X-ray detector to acquire a plurality of projection images at different angulations. A graphical display is configured to present graphical images. A control unit is communicatively connected to the acquisition unit. The control unit operates the acquisition unit to acquire the plurality of projection images. The control unit processes the plurality of projection images to produce a plurality of FFDM images. The control unit is communicatively connected to the graphical display to visually present at least one synthetic stereo image from the plurality of synthetic stereo images on the graphical display. A biopsy robot is communicatively connected to the control unit. The control unit receives a user input of a biopsy location based upon the visually presented at least one synthetic stereo image. The control unit operates the biopsy robot to biopsy the biopsy location.

An exemplary embodiment of a method of controlling a needle biopsy includes receiving a plurality of tomographic projection images. A 3D volume is reconstructed from the plurality of tomographic projection images. A plurality of synthetic stereo images are produced from the plurality of tomographic projection images. These synthetic stereo images are presented on a graphical display to a clinician for receiving at least one input for biopsy control. A user input of a location to biopsy is received in at least one of the synthetic stereo images. A biopsy robot is operated to move a tip of a biopsy needle to the location.

DETAILED DISCLOSURE

Figure 1:
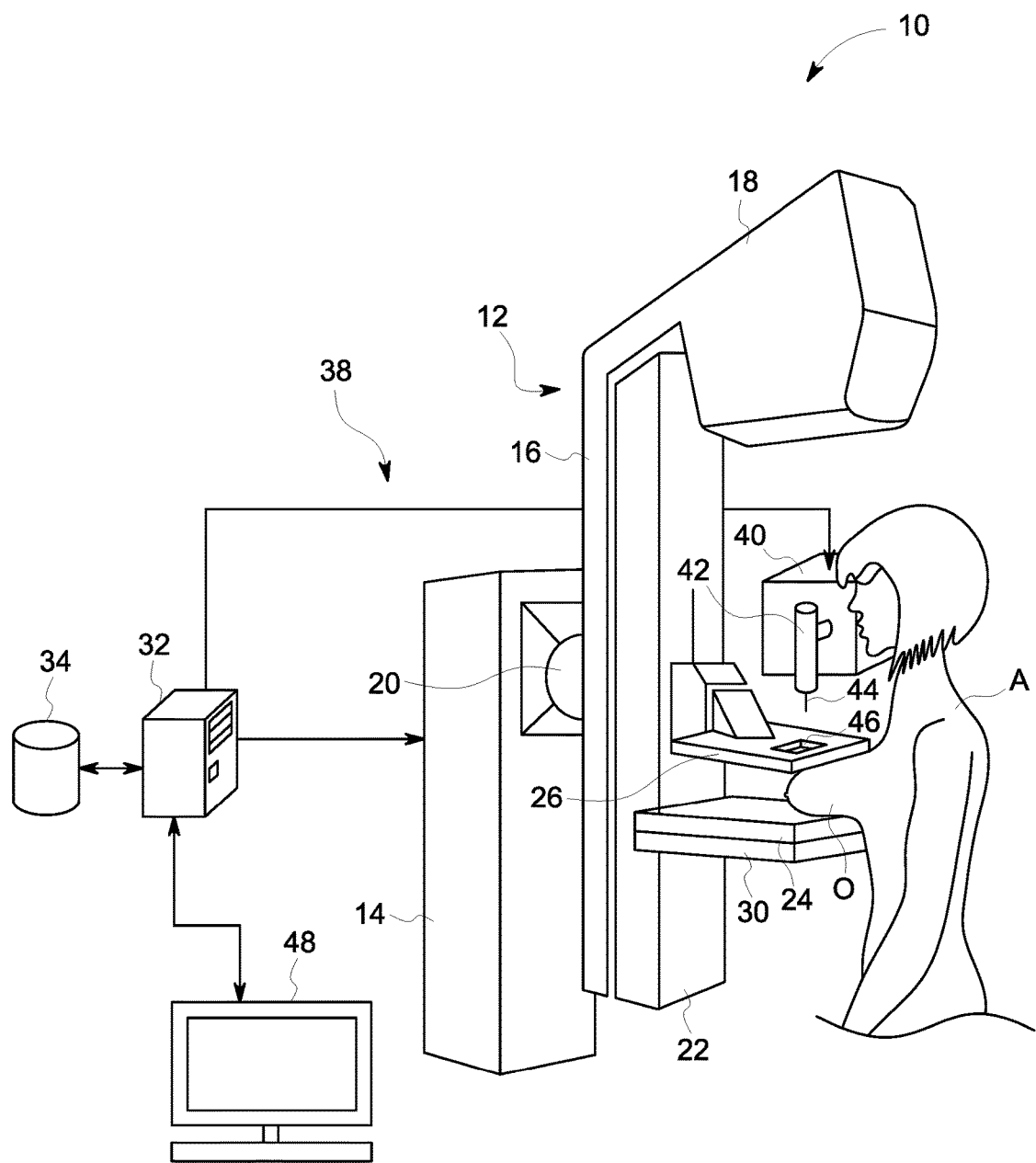
FIG. 1 depicts an exemplary embodiment of a biopsy system.

FIG. 1 depicts an exemplary embodiment of a biopsy system 10. The biopsy system 10 exemplarily includes a medical imaging system 38 and a biopsy robot 40. The medical imaging system 38 operates in the manners as described herein in order to create synthetic digital mammography images which may be used to create improved control of a biopsy needle for use in a biopsy of a breast. The medical imaging system 38, as described in further detail herein enables the acquisition of 2D projection images of a tissue matrix of an organ O, exemplarily a breast of a patient A. The medical imaging system 38 processes the 2D projection images as described in further detail to create synthetic digital mammography images to facilitate needle positioning by the biopsy robot and locating a biopsy target, for example a center of a lesion within the breast.

The medical imaging system 38 includes an acquisition unit 12 which operates to acquire the 2D projection images. The acquisition unit 12 exemplarily includes a vertical stand 14 and a positioning arm 16 which includes a radiation source 18 e.g. an X-ray emitter. The positioning arm 16 is exemplarily rotationally joined to the vertical stand 14 about a rotation shaft 20. The vertical stand 14 is fixed. Therefore, by moving the positioning arm 16, the radiation source 18 can be positioned at various orientations about the rotation shaft 20.

The acquisition unit 12 further includes a support arm 22. The support arm exemplarily includes a detector support 24 and a compression paddle 26. The detector support 24 is configured to support the organ O from below and exemplarily includes an X-ray detector as described in further detail herein. The compression paddle 26 is generally parallel to the detector support 24 and is generally translatable to various positions along a translation rail 28 relative to the detector support 24. The compression paddle 26 exemplarily moves towards the detector support 24 to compress the breast O against the detector support 24 for medical imaging. Compression of the breast between the detector support 24 and the compression paddle 26 keeps the breast O immobile during the acquisition of medical images and improves uniformity of the tissue matrix which improves imaging. During a biopsy, compression of the breast further helps to create uniformity of the tissue matrix which improves insertion of the needle and locating of the needle once it is inserted into the tissue. The detector support 24 further includes an anti-diffusion grid 30 which exemplarily includes a plurality of opaque components arranged in parallel to one another, in a direction parallel to the motion of the positioning arm and operates to limit the impact and spread of emitted X-rays within the body of the patient A.

The positioning arm 16 and the support arm 22 may be joined to one another or may be separate components, allowing their rotation relative to each other about the rotation shaft 20. In still further embodiments, the detector support 24 may be translatable and/or rotatable in order to accommodate a height of the patient. In still further embodiments, while not depicted, the acquisition unit 12 may include a lower support that supports the breast O while the detector 24 is connected to the positioning arm 16 for coordinated movement between the detector 24 and the radiation source 18. In other embodiments, the X-ray emitter within the radiation source 18 may correspondingly adjust the X-ray beam emitted from the radiation source 18 such as to maintain the breast O in the X-ray beam while keeping the X-ray beam in alignment with the detector 24 to maximize the part of the X-ray radiation emitted by the radiation source 18 that impinges upon the detector 24. The detector 24 may include a semi conductor image sensor containing cesium iodide phosphor for example (scintillator) on a transistor/photodiode array in amorphous silicon. Other suitable, but not limiting, detector is a CCD sensor a direct digital detector which directly converts X-rays into digital signals. While the detector 24 illustrated in FIG. 1 is planar and defines a planar image surface, other geometries will be recognized as being suitable depending upon the acquisition unit 12, including, but not limited to digital X-ray detectors of curved shape forming a curved image surface.

The detector exemplarily located within the detector support 24 is exemplarily an array formed by a plurality of detector rows (not shown) including a plurality of detector elements which together sense the projected X-rays that pass through the object O. Each detector element of the detector array produces an electrical signal that represents the intensity of an impinging X-ray beam and hence the attenuation of the beam as it passes through the object O. While the Figures as shown and described herein may only show a single row of a detector ray or detector elements, it will be recognized that the detector includes a plurality of parallel rows of detector elements so that projection data corresponding to a plurality of quasi-parallel or parallel slices can be acquired simultaneously during a scan. The control unit 32 provides power and timing signals to both the X-ray source 18 and the detector such that a data acquisition system of the control unit 32 samples the X-ray data from the detector elements and converts the data to digital signals for subsequent processing.

The imaging system 10 further includes a control unit 32 connected to the acquisition unit 12 either by wired or wireless communicative connections. The control unit 32 sends electric control signals to the acquisition 12 to set several parameters such as the radiation dose to be emitted, the angle and/or position of the positioning arm 16, the angle and/or positioning of the support arm 22, and the angle and/or position of the detector support 24 and/or compression support 26. The control unit 32 may include computer memory or a reader device for reading data and/or computer code stored on computer memory, for example magnetic or solid state memory devices, or other removable computer readable media which may be read by the control unit 32 to access computer readable code with instructions of the methods as described herein. The control unit 32 may be implemented on one or more computer processors that may further include a communicative connection, wither wired or wirelessly, to a memory unit 34 which may be a ROM/RAM memory of the control unit 32, a USB flash drive, memory card, or computer memory of a networked server. The control unit 32 operates to record parameters and/or required images in the computer memory 34.

In an exemplary embodiment, the control unit 32 also operates as an image processing unit. In alternative embodiments, the image processing unit may be embodied as a separate processor. In a still further embodiment, the control unit 32 and the image processing unit may be embodied in multiple processors and/or one or more remotely located or cloud-based processors. The image processing unit receives the medical images acquired by the acquisition unit 12 under the operation of the control unit 32 and processes the acquired medical images in the manners as described herein through execution of computer readable code stored on a non-transient computer readable medium communicatively connected to the control unit 32 upon which such computer readable code is stored. Execution of the computer readable code by the control unit 32 causes the control unit 32 to carry out the functions and operations as described in further detail herein. The control unit 32 operates to store the processed medical images and further medical images as generated through the operation of the control unit on the computer memory 34. Although it will be understood that in embodiments, computer memory 34 may be multiple memory devices which may further be located at different locations.

As will be described in further detail herein, the control unit 32 is further connected to a biopsy robot 40. The biopsy robot 40 includes a motor (not depicted) and an articulable arm 42 to which a needle 44 is secured. By way of commands and inputs from the control unit 32, the biopsy robot 40 moves the articulable arm 42 and the needle 44 to insert the needle into the tissue of the patient, e.g. the patient's breast to perform a biopsy of tissue as described herein for use in the diagnosis of breast cancer. A biopsy window 46 may be located through the compression paddle 26. The biopsy window 46 provides access to the breast for the needle 44, while maintaining the breast under compression.

The control unit 32 and the image processing unit 36 are both connected to a graphical display 36 which may further incorporate a user input device. In an exemplary embodiment, the graphical display may be a touch sensitive graphical display and operate as both the graphical display and the user input device. While in still further embodiments, the user input device may further include, but is not limited to keyboard, push buttons, touch screen displays with graphical user interfaces (GUI), or any of a combination of the above or other input devices as will be recognized by one of ordinary skill in the art.

The input device 40 is operated by a clinician or technician to input control commands and/or processing commands and to interact with the medical images as generated by the imaging system 10. In an exemplary embodiment, the input device 40 may be a part of or associated with a graphical display 48 to which the control unit 32 is connected. The graphical display 48 is operated to present one or more graphical user interfaces (GUI) to visually present information regarding the acquisition of medical images by the acquisition unit 12 and/or to present the acquired medical images or the medical images as generated by the control unit 32 operating as an image processing unit as will be described in further detail herein. It will also be recognized that while graphical display 48 is depicted as a single graphical display, that multiple graphical displays and/or graphical displays located at different locations, including, but not limited to mobile devices may be used in implementing various embodiments of the systems and methods as disclosed herein.

Figure 2:
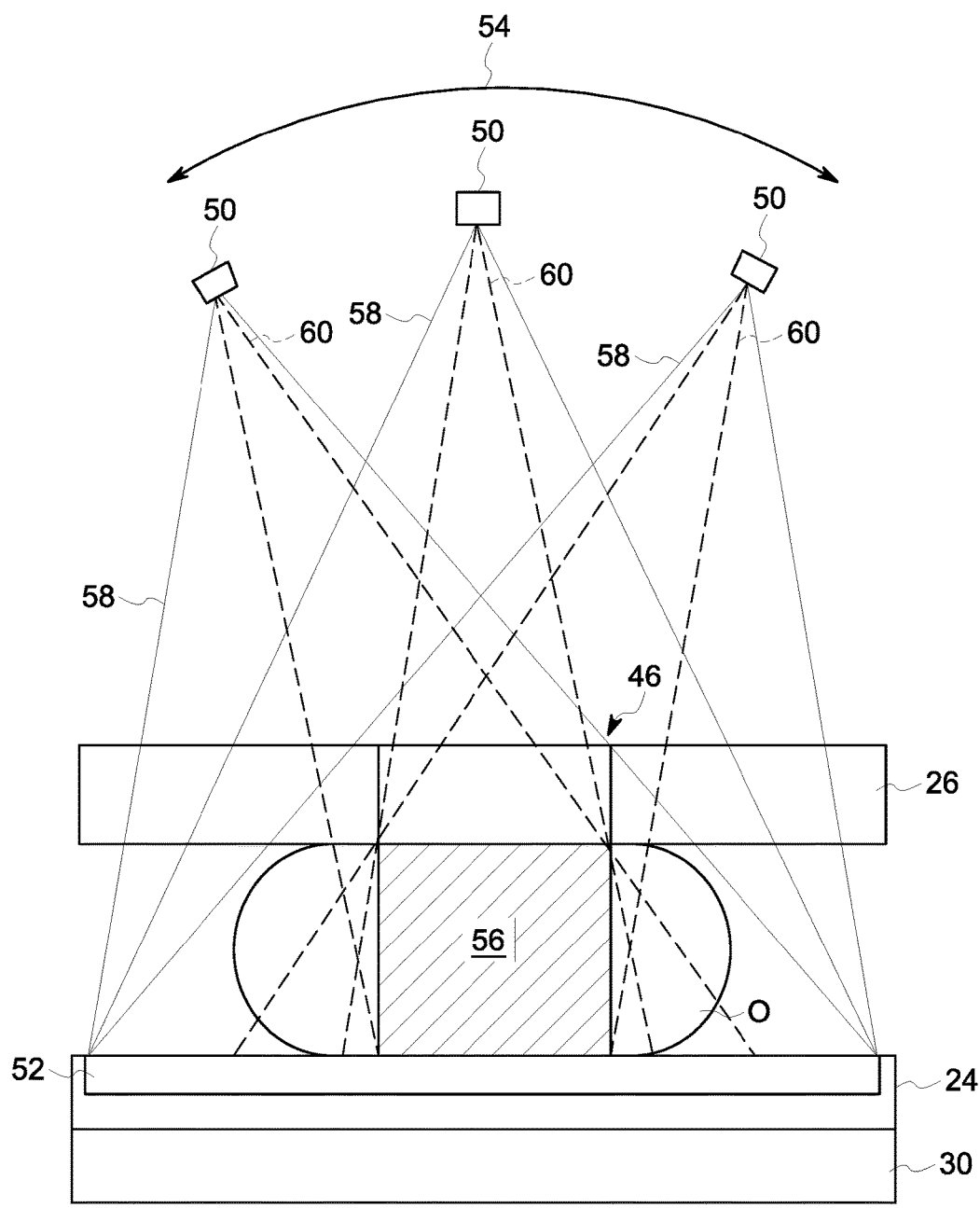
FIG. 2 diagrammatically depicts acquisition of a plurality of digital breast tomography projection images.

FIG. 2 diagrammatically depicts acquisition of a plurality of tomographic (e.g. digital breast tomography (DBT) projection images. In FIG. 2 a patient's breast O is compressed between the compression paddle 26 and the detector support 24. As described above, an anti-diffusion grid 30 is located below the detector 24 to limit the effects of X-ray radiation on the rest of the patient's body. FIG. 2 depicts an X-ray emitter 50 (which is exemplarily located within the radiation source 18 of the acquisition unit 12 as shown in FIG. 1) located at a variety of positions relative to the patient's breast O. The control unit (not depicted) may provide positioning signals to the positioning arm (not depicted) to adjust the position of the X-ray emitter 50. The control unit may further provide control instructions to the radiation source to control the shape and/or strength of the X-ray beam emitted from the X-ray emitter 50 at each of the plurality of positions. In an exemplary embodiment, the emitted X-ray beams may be shaped to adjust for a stationary detector support 24 and a moveable X-ray emitter 50 such as to maximize the X-ray beam that impinges on both the breast O and the detector 52 contained within the detector support 24. The detector 52 detects the radiation passing through the breast O, and the control unit stores the image read on the detector 52 in the memory unit. In embodiments, the control unit further stores the position of the X-ray emitter 50 used to acquire each of the projection images and/or the position of the detector (e.g. via the position of the detector support 24 in the embodiment depicted). This acquisition operation is repeated for several positions of the X-ray emitter 50 about the breast O. In an exemplary embodiment, the positions of the X-ray emitter are evenly spread across an acquisition geometry 54. In an exemplary embodiment, the acquisition geometry 54 may exemplarily be an arc, linear, or any other (including more complex) geometry. The acquisition geometry 54 may exemplarily be 20° of arc, 25° of arc, 30° of arc, 40° of arc, or 60° of arc. It will be understood that these sizes of the acquisition geometry 54 are exemplary in nature and that other acquisition geometry shapes and sizes may be used as will be recognized by a person of ordinary skill in the art in view of the present disclosure.

In the exemplary embodiment depicted, three positions of the X-ray emitter 50 are shown for the sake of conciseness, but it will be recognized that during a DBT imaging process, a plurality of projection images each taken at a different position of the X-ray emitter 50 are acquired by the acquisition unit. In one exemplary embodiment, nine projection images are acquired during a DBT imaging process, although it will be recognized that in other embodiments more or fewer projection images may be acquired. As noted above, if nine tomographic projection images are acquired, the radiation dose for each of the tomographic projection images will typically be one ninth of a standard radiation dose of a full field digital mammogram (FFDM) image. In the exemplary embodiment wherein nine projection images are acquired, one of the projection images will typically be acquired from a position normal to the center of the detector in the detector support and representative of zero degrees of arc along the acquisition geometry 54. The other X-ray emitter positions may be evenly spaced in either direction along the acquisition geometry from this center image. As the X-ray emitter 50 is moved relative to the breast O, the control unit may operate the X-ray emitter 50 to shape the X-ray beam 58 from the X-ray emitter 50 to maintain the X-ray beam 58 focused on the breast O and the detector 52. It will be recognized that in still further embodiments, the detector 52 and detector support 24 may be rotated and the center image position of the X-ray emitter as well as the acquisition geometry 54 may be rotated to maintain this relationship between the X-ray emitter positions along the acquisition geometry 54 and the detector in the detector support 24 relative to the patient's breast O.

Figure 3:
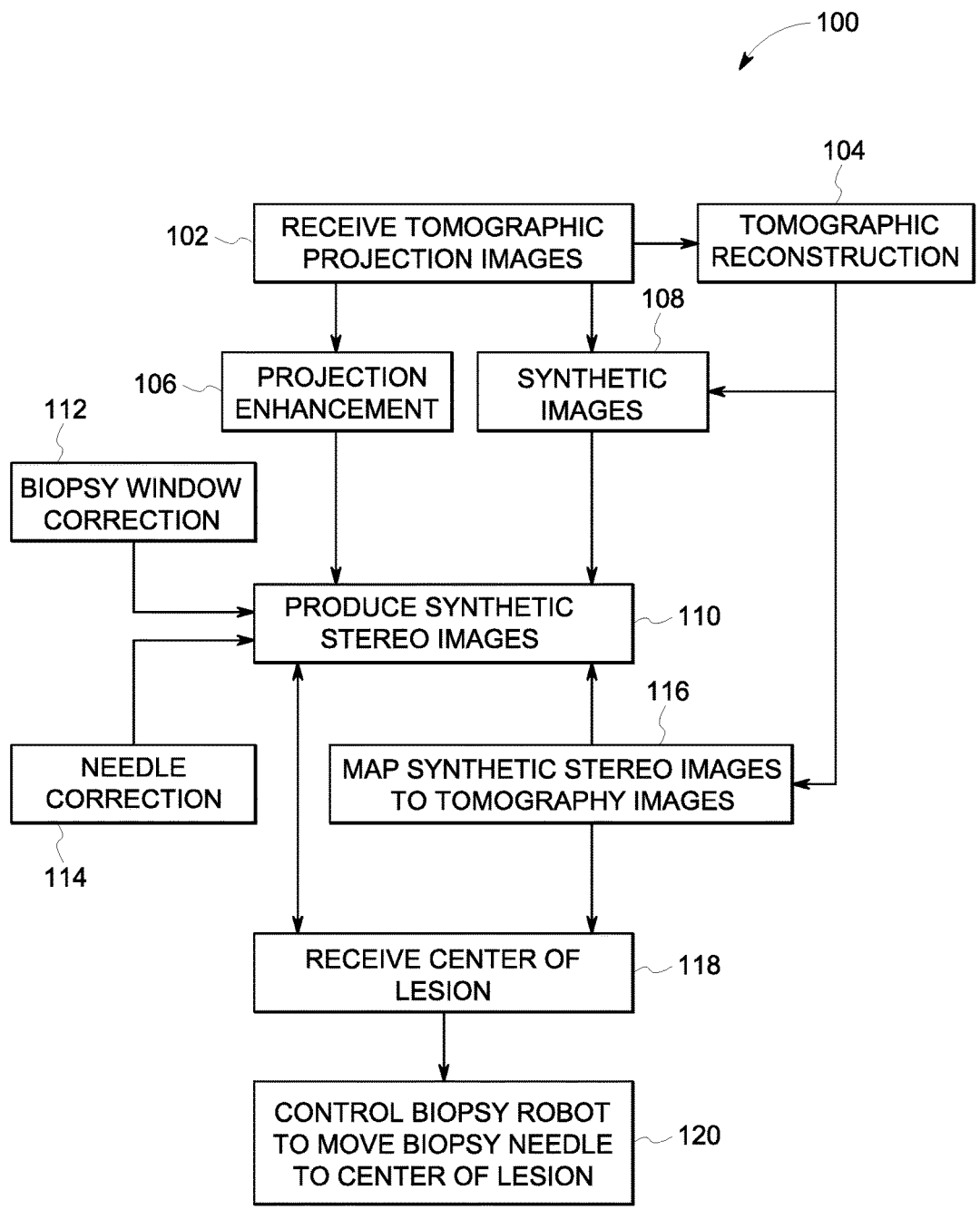
FIG. 3 is a flow chart that depicts an exemplary embodiment of a method of biopsy control

FIG. 3 is a flow chart that depicts an exemplary embodiment of a method 100 of biopsy control. The method 100 begins at 102 wherein a plurality of tomographic projection images are received. In an exemplary embodiment, the plurality of tomographic images are obtained by an image acquisition unit as previously described while in other embodiments, the method 100 may be implemented on a computer system separate from the image acquisition unit and therefore receive the images as acquired by a separate device. In an exemplary embodiment, the plurality of tomographic projection images includes nine projection images while it will be recognized that other numbers of projection images may be received while remaining within the scope of the present disclosure. In an exemplary embodiment if the dose associated with a typical FFDM imaging procedure for guiding a needle biopsy is an amount D, the radiation dose for each of the acquired projection images of the plurality of tomographic projection images is D/N wherein N is the number of projection of images in the plurality. In this exemplary embodiment, it will be recognized that the plurality of tomographic images are acquired using the same or less than radiation dose as a comparable FFDM procedure. As will be recognized, due to the lower dose per image acquired, the contrast to noise ratio in each of the received tomographic projection image is less than the contrast to noise ratio of a similarly positioned FFDM image.

At 104 the received tomographic projection images are used to produce a tomographic reconstruction at 104. The tomographic reconstruction produces a plurality of three dimensional slices of a predetermined thickness. However, as referenced above, in the context of tomosynthesis guided biopsy, the tomographic reconstructed slices present a challenge during a control of a needle biopsy when the lesions are spread over several consecutive slices, including an example in which a cluster of calcifications are located across a plurality of tomographic slices. Thus, additional angulated 2D views can provide a clinician with additional information and context in order to properly control the biopsy procedure. Additionally, the angulated 2D views are desired to be acquired without exposing the patient to additional radiation doses. Therefore, at 106 and 108 one or more synthetic angulated 2D stereo views are constructed from the tomographic projected images. At 106, the synthetic stereo images are produced by enhancing the image quality of one or more of the received tomographic projection images using the information contained in the other projections. At 108 one or more synthetic images are created in a virtual acquisition from the tomographic reconstruction. Exemplary embodiments of these two techniques will be described in further detail herein. Either enhancement of projection images from 106 or creation of synthetic images at 108 are used to produce synthetic stereo images at 110. The synthetic stereo images are from at least two different angles relative to the patient's breast. In the exemplary embodiment wherein tomographic projection images are enhanced to produce these synthetic stereo images the angle of the synthetic stereo images will be selected from the angles of the underlying tomographic projection images. If synthetic images are produced, then the synthetic stereo images will be at predetermined or user selected angles from which the synthetic stereo images are created.

While the above-noted steps may produce synthetic stereo images at 110, in the control of a needle biopsy, further directions and/or biopsy specific information may be incorporated into the synthetic stereo images produced at 110 to improve the resulting images for use in biopsy control. Specifically, a field of view correction at 112 corrects for artifacts introduced by the biopsy window in the compression paddle as well as the paddle borders. Referring back to FIG. 2, the biopsy window 46 through the compression paddle 26 creates an artifact or discontinuity as some of the X-rays from the emitter 50 pass through the biopsy window 46 and other X-ray from the emitter 50 pass with more difficulty through the compression paddle 26 before passing through the breast O and imaging upon the detector 52. Therefore, while X-rays that pass through the compression paddle 26 are attenuated compared to those X-rays that pass through the biopsy window 46.

In exemplary embodiments, these paddle artifacts including those due to the biopsy window 46 may be smoothed or corrected in the tomographic projection images prior to producing the synthetic stereo images at 110. Furthermore, as depicted in FIG. 2, a biopsy needle is inserted into the patient's breast O while the breast O is kept under compression by the compression paddle 26. The biopsy needle is inserted through the biopsy window 46, thus the biopsy window 46 generally define a region 56 of the breast O within which the needle biopsy can be performed. Thus, the synthetic stereo images can be further refined to only show the region of interest 56. In an exemplary embodiment, this may be done by only producing synthetic stereo images of the region of interest, but basing such synthetic stereo images on all of the tomographic projection image data, or by restriction the image data of the tomographic projection images to only those portions of the tomographic images that contain information related to the region of interest. In a further exemplary embodiment, a field of view, exemplarily commensurate in size with the region of interest 56 is determined for each of the plurality of tomosynthesis projection images. During the 3D reconstruction process and/or the synthetic 2D generation process, the areas outside of the field of view may be discarded from at least one of the plurality of tomosynthesis projection images, and in an embodiment all of the tomosynthesis images used to produce the synthetic stereo images except the projection corresponding to the synthetic stereo image. As depicted in FIG. 2, a full field X-ray beam 56 is shown in solid lines from each of the positions of the emitter 50. While a reduced field is identified in the dashed lines at 60 which represents the image data which contains information regarding the tissue matrix within the region of interest 56.

Figure 4:
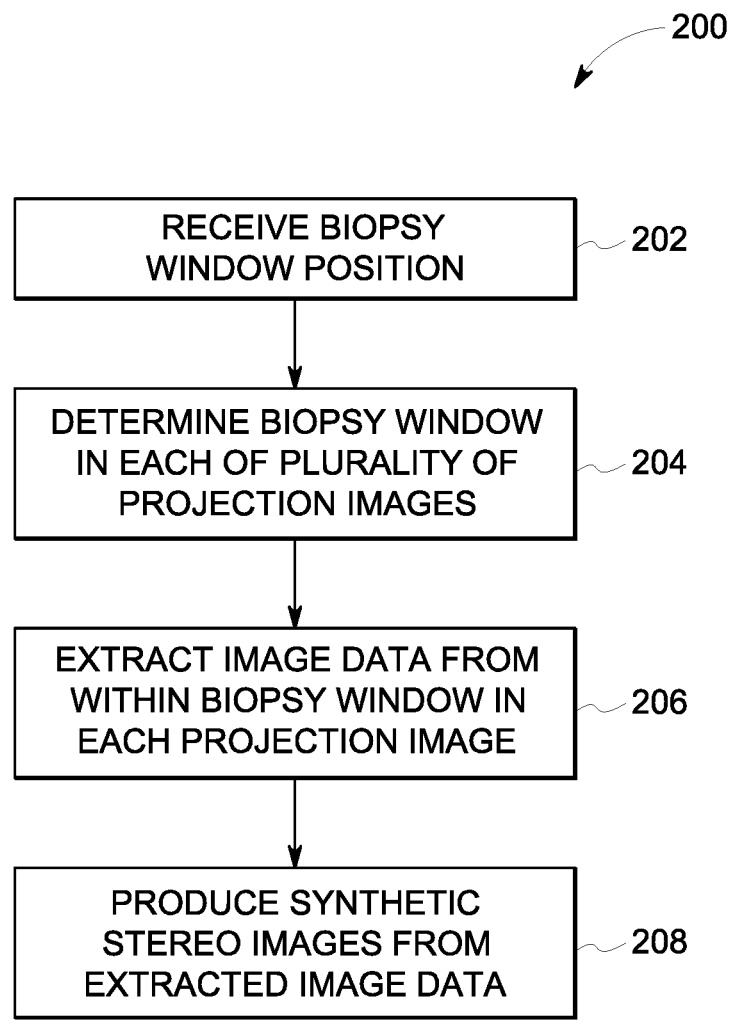
FIG. 4 is a flowchart that depicts an exemplary embodiment of a method of biopsy window correction.

FIG. 4 is a flowchart that depicts an exemplary embodiment of a method 200 of biopsy window correction in the manner as described above. It will be recognized while the example of a biopsy window correction is used herein, that other exemplary embodiments the images may be corrected by similar methods as described herein to correct for artifacts from a paddle area or an intermediate field of view. In still further exemplary embodiments, methods as disclosed herein may be used to correct for artifacts exemplarily from a needle, biopsy gun, biopsy positioner, or a metallic frame of a paddle, or other objects as will be recognized by a person of ordinary skill in the art from the present disclosure.

The method 200 begins by receiving information identifying a biopsy window position. In an exemplary embodiment, this information may come from the acquisition unit in that a position of the compression paddle is known and a position of the biopsy window within the compression paddle is similarly known. Furthermore, as a geometric relationship between the emitter at acquisition of each of the projection images and the compression paddle and biopsy window in the compression paddle are known, this information can identify the biopsy window position in every tomosynthesis projection image.

At 204 the biopsy window position is determined in each of the plurality of projection images. With the known location of the biopsy window at acquisition of the projection image, an expected location of the biopsy window can be determined for the projection image. In another exemplary embodiment, an automated image processing software and/or algorithm may detect the biopsy window artifact and use this detection to identify the biopsy window in the projection image.

At 206, the image data from within the biopsy window may be extracted from each of the projection images. As mentioned above, while there are a variety of ways in which the biopsy window may be corrected for, one such technique extracts image data from within the biopsy window for further analysis at 206 and at 208 uses this extracted image data to produce the 3D volume and/or synthetic stereo images. By limiting the image data to only the image data which contains information regarding the region of interest within the area of the biopsy window, then there are less sources for the introduction of further artifacts, including removing or substantially removing paddle artifacts which include those attributable to the attenuation discontinuity created by the biopsy window.

Returning back to FIG. 3, in another exemplary embodiment, if the tomographic projection images are acquired while the biopsy needle is inserted into the patient, the biopsy needle itself may be identified and attenuated in order to reduce and/or remove metallic and/or other artifacts as caused by the needle itself in the acquired tomographic projection images. In an exemplary embodiment, the biopsy needle may be detected in each of the tomographic projection images for example using image processing techniques. In an exemplary embodiment, a biopsy needle is typically constructed of a comparatively radiopaque material, for example medical grade stainless steel and therefore will often appear with great contrast to that of the surrounding breast issue. Once detected in each image, the image of the needle may be removed, obscured or otherwise attenuated or less magnified than other image areas in a way such as to reduce reconstruction artifacts of the needle in the processed tomographic reconstruction and/or synthetic stereo images. While the biopsy needle may be removed or attenuated in the tomographic projection images used to produce the synthetic stereo images at 110, the coordinates and orientation of the biopsy needle may be identified and retained such that a reconstruction of the biopsy needle may be overlaid in the synthetic stereo images and/or tomographic reconstruction. In a non-limiting embodiment, the instrument may be reconstructed in the synthetic stereo images and/or tomographic reconstruction by way of intersection of back projection planes, while it will be recognized by persons of ordinary skill in the art that other techniques for instrument reconstruction may be used.

As previously mentioned, clinicians may use the tomographic reconstruction from 104 in controlling the location of the biopsy to be performed. While in some clinical cases, the size, shape, and location of the lesion and/or groupings of calcifications may results in the clinician requiring additional information in the form of 2D projection views to refine and/or confirm biopsy needle control. Therefore, in an exemplary embodiment, the synthetic stereo images produced at 110 may be mapped at 116 to the tomographic reconstruction 104. This mapping between the synthetic stereo images and the tomographic reconstruction enables navigation by the clinician between the synthetic stereo images and the tomographic reconstruction. Such a navigation map enables the clinician to switch between coordinated views of the 2D synthetic stereo images to an associated tomographic reconstruction plane that contains the same selected anatomical feature. Thus, the clinician, being presented with one of the 2D synthetic stereo images on a graphical display, can select the center of a lesion in one of the synthetic stereo images. This user selection of the center of the lesion can be received by the system at 118 and the clinician can confirm the selection of this point for the needle biopsy by the system switching the visual presentation on the graphical display to a view of the selected point in the associated tomographic reconstructed plane. A similar embodiment would work in reverse wherein clinician may select a point in a plane of the tomographic reconstruction presented on the graphical display and similarly navigate to a visual presentation of one of more of the produced synthetic stereo images with the same center point identified using a reprojection operator on the graphical display in order for the clinician to confirm the selection of the target for biopsy. Moreover, upon receiving a new location to update the position of the center point in the identified plane or in the synthetic stereo images, the new location is automatically updated in the identified plane and in the synthetic stereo images.

After the system receives an indication of the center of the lesion at 118, the system may control the biopsy robot to move the biopsy needle target at 120.

Synthetic stereo images may be produced by enhancing one or more of the received tomographic projection images with information provided by the other tomographic images. This is previously described above with respect to 106 in the method 100 of biopsy control, depicted in FIG. 3. In an exemplary embodiment, the synthetic stereo images may be produced in the following manner.

After the tomographic projection images are received, a filter is applied to the tomographic projection images so as to obtain filtered projection images of the object of interest O. This filter is preferably of the high-pass type and its cut-off frequency is preferably a function of the thickness of the object of interest O. Next, slices are determined for reconstructing the object of interest O. This determination may include a backprojection of the filtered 2D projection images. This back projection may in particular be non-linear of the "Order Statistics Based Backprojection" type. In the linear back projection, each voxel of the volume is reconstructed by using N information pixels, each pixel being determined by backprojection of the voxel in each of the N projections. In the non-linear backprojection, the maximum intensity pixel among the N pixels is not used, which allows significant reduction of the replication artifacts caused by the most intense objects. As would be recognized by a person of ordinary skill in the art, it is noted that the slices for reconstructing the object of interest O represent the reconstructed volume of the object of interest O.

Next, a reprojection of the reconstruction slices is carried out in the determined direction of the tomographic projection image to be enhanced into the synthetic stereo image. With this, it is possible to obtain an intermediate 2D image of the object of interest O. It is noted that reprojection occurs along the same direction as the projection image corresponding to the determined orientation. A final 2D image of the object of interest is obtained by combining the intermediate 2D image and the projection image corresponding to the determined orientation. The combination is preferably a pixel-to-pixel linear combination. It will be recognized that the step of re-projection may be performed using any number of known reprojection techniques, including, but not limited Maximum Intensity Pixel (MIP) or Sorted Intensity Pixel (SIP), as well as others as will be recognized by one of ordinary skill in the art. The height providing the MIP or SIP in each pixel (i,j) provides the navigational map at (i,j). Additionally, these examples of using projection image enhancement to create the synthetic stereo images are merely exemplary and a person of ordinary skill in the art will recognize other techniques as may be used within the scope of the present disclosure.

As discussed above, in exemplary embodiments, a synthetic 2D image is reconstructed from at least one baseline image. The selected baseline image is enhanced with pixel information from the 2D tomosynthesis projection images. For each pixel (i,j) of the baseline image and for a given height, the algorithm accumulates the values of the corresponding pixel position in at least one of the filtered tomosynthesis projections. A ranking of the accumulated values for each pixel over all possible heights is performed. The most likely height for each pixel (i,j) by selecting the maximum accumulated value is determined. The most likely height in each pixel (i,j) provides the navigational map at (i,j). Each baseline image pixel (i,j)'s level is combined with the determined maximum values.

In exemplary embodiments, the baseline image is enhanced using at least a subset of the plurality of the tomosynthesis projection images. In a particular embodiment, a set of synthetic stereo images are generated by enhancing the following baseline images: the extreme angulations of the tomosynthesis acquisition and/or the projection perpendicular to the detector. The angulated synthetic stereo images allow better visualizing clusters of calcification, needle in place. The synthetic perpendicular projection allows to appreciate if the lesion in under the biopsy window. The baseline image may be obtained from a volume representing the object that was originally acquired using at least a reprojection operator. In exemplary embodiments, this volume may or may not be a reconstruction of the input tomosynthesis projection images. In other embodiments, the volume may exemplarily be a volume from CEDBT or an ultrasound volume. In an exemplary embodiment, the baseline image is obtained by interpolating a subset of the plurality of tomosynthesis projection images. In another exemplary embodiment, the baseline image is at least one image selected from the plurality of tomosynthesis projection images. In an embodiment, the at least one projection image may be selected by filtering at least a subset of the tomosynthesis projection images and reconstructing a volume from the filtered projection images. The volume is reprojected and the volume reprojection is combined with a selected projection or a filtered version of the selected projection. In a still further exemplary embodiment, a field of view is determined in the baseline image and the baseline image is enhanced in the area within the field of view.

Figure 5:
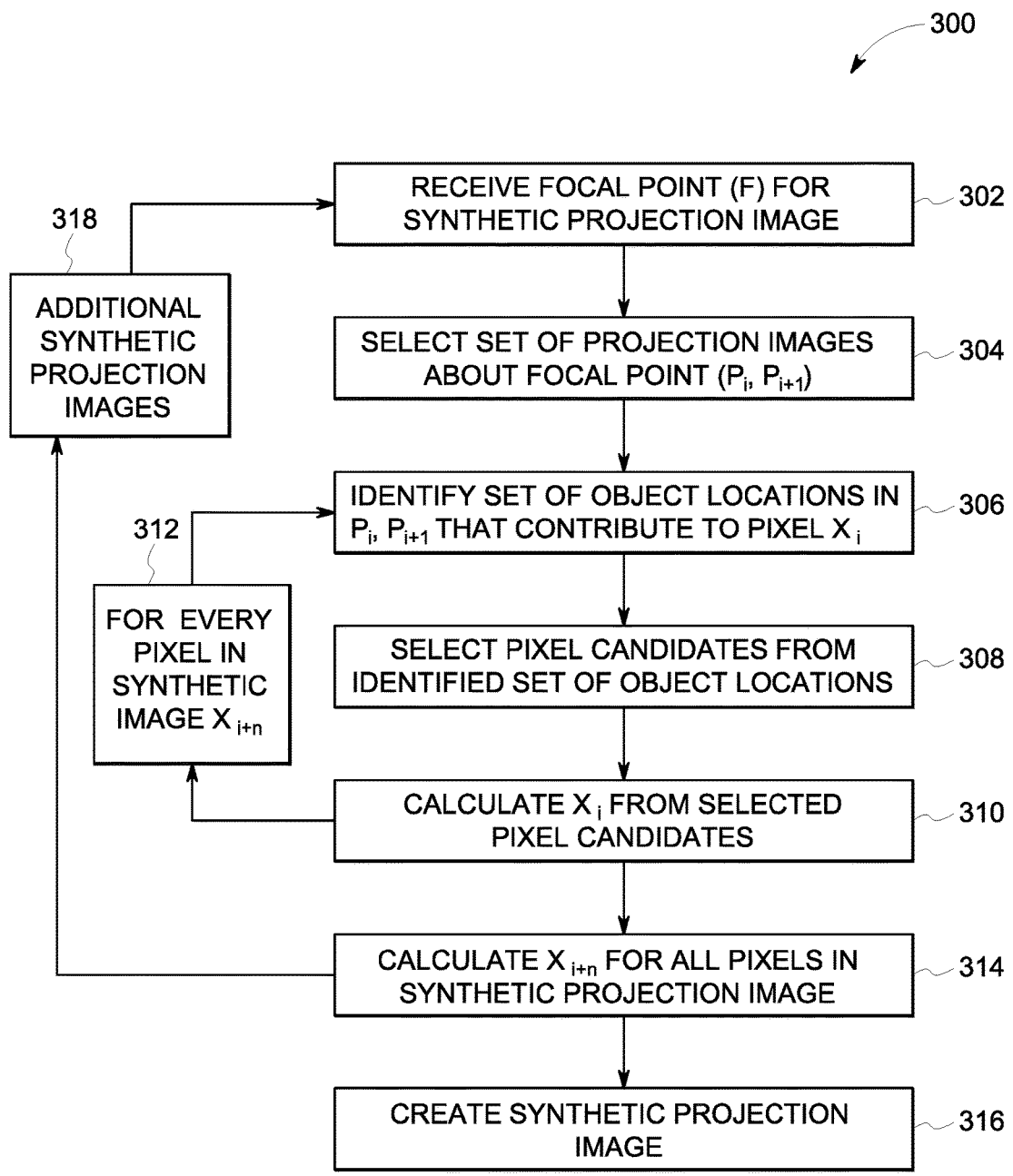
FIG. 5 is a flow chart that depicts an exemplary embodiment of a method of creating synthetic projection images.

FIG. 5 is a flow chart that depicts an exemplary embodiment of a method 300 of creating synthetic projection images, as may be exemplarily used at 108 of the method 100 of FIG. 3. As described in further detail herein the method 300 functions to create a synthetic projection image exemplarily from a focal point different from any of the focal points of the positions of the X-ray emitter used to acquire the plurality of tomographic projection images.

The method 300 continues at 302 when the processing unit receives a focal point F for a synthetic projection image. The received focal point F may exemplarily be received through the input device of the system and exemplarily identifies a focal point that is different from any of the focal points or X-ray emitter positions at which the DBT projection images were acquired. Additionally, the received focal point is exemplarily located between the positions of two adjacent acquired DBT projection images. At 104, the image processing unit selects a set of projection images about the received focal point.

In an exemplary embodiment the set of projection images may include at least two projection images. The projection images may include the acquired DBT projection images and/or may include previously created synthetic projection images. In an embodiment as explained in further detail herein, the set of projection images may include all of the available projection images. In one exemplary embodiment, the set of projection images includes a first projection image and a second projection image for the acquired DBT projection images, for example the DBT projection images nearest to or immediately adjacent to the received focal point. In another exemplary embodiment one or both of the first projection image and the second projection image in the set of projection images is a synthetic projection image that is nearest to the received focal point.

Figure 6:
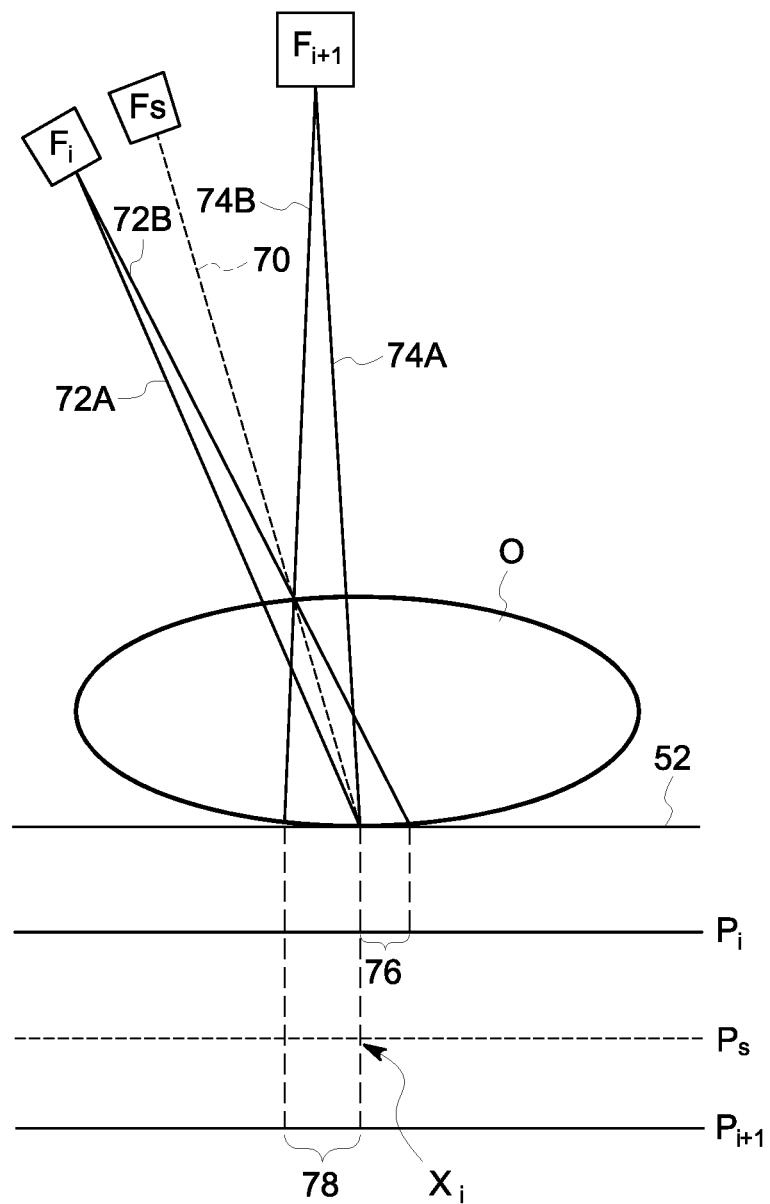
FIG. 6 diagrammatically depicts the interpolation of a synthetic projection image of object according to the method.

FIG. 6 diagrammatically depicts the interpolation of a synthetic projection image of object O according to the method 300 as described herein. In FIG. 6, the patient's breast O is positioned adjacent the X-ray detector 52. $F_i$ and $F_{i+1}$ represent the X-ray emitter positions respectively used to acquire corresponding DBT projection images $P_i$ and $P_{i+1}$. The received focal point $F_s$ represents an artificial X-ray emitter position located between the positions $F_i$ and $F_{i+1}$ from which the synthetic projection image $P_s$ will be generated. As noted above, while FIG. 4 shows the acquired projection images $P_i$ and $P_{i+1}$ and the synthetic projection image $P_s$ as lines or rows of pixels, it will be recognized that the actual acquired projection images and synthetic projection images are two dimensional and will constitute a plurality of rows of pixels and that the process as described herein may be repeated across all of the rows of pixels to create a 2D synthetic projection image. In still further exemplary embodiments as described herein, each pixel in the 2D synthetic projection image is processed in parallel.

As depicted in FIG. 6, pixel $X_i$ of the synthetic projection image $P_s$ is the pixel to be created and is represented by the dotted projection line 50 from the focal point $F_s$ through the breast O to the X-ray detector 52. The pixel $X_i$ in the synthetic projection image $P_s$ contains information from all points through the tissue matrix of the breast O along the projection line 70. Respective projection lines 72A and 74A are respectively from focal point $F_i$ and $F_{i+1}$ intersect with projection line 70 where projection line 70 exits the breast O. Similarly, projection lines 72B and 74B respectively from focal point $F_i$ and $F_{i+1}$ intersect projection line 70 at the location where projection line 70 enters the breast O. The points where the projection lines 72A and 72B from focal point $F_i$ hit the detector 52 define the portion 76 of projection image $P_i$ in which information regarding the tissue matrix of the breast O represented in pixel $X_i$ can be found. Similarly, the locations where projection lines 74A and 74B from the focal point $F_{i+1}$ hit the detector 52 define the portion 78 of the projection image $P_{i+1}$ which contains information regarding the tissue matrix of the breast O represented in pixel $X_i$.

Referring back to FIG. 5, the description of which will also refer to FIG. 6 and will focus on an exemplary embodiment in which the set of projection images is made up of a first projection image and a second projection image. It will be recognized from the present disclosure that this process is not so limited and sets of projection images having other numbers of acquired and/or synthetic projection images may be used. At 306 the set of object locations in the projection images $P_i$ and $P_{i+1}$ of the set of projection images that contribute to pixel $X_i$ are identified. These are respectively the portion 76 of a projection image $P_i$ and portion 78 of projection image $P_{i+1}$ identified in FIG. 6. Once these sets of object locations are identified, then pixel candidates from the identified sets of object locations are selected at 308. The selected pixel candidates at 308 represent the best candidate pair of pixels from the projection image $P_i$ and $P_{i+1}$ to represent the information in pixel $X_i$ of the synthetic projection image $P_s$. This can be represented in a general case which is applicable to sets of any number of projection images as:

$$[v]=C(v_i, v_{i+1}) \tag{1a}$$

While in the specific exemplary core of a set of projection images having two projection images is represented as:

$$v=\mathrm{argmax}_{v \in V} C(v_i, v_{i+1}) \tag{1b}$$

where V is the set of tissue matrix locations contributing to the value of $X_i$ and $v_i$ is the projection of voxel V on the projection image $P_i$ and $v_{i+1}$ is the projection of voxel V on the acquired projection image $P_{i+1}$.

C is a criterion function for selection of the voxel V of the set of tissue matrix locations contributing to the value of X (e.g. along projection line 70) that is a good candidate for interpolating the value of X. Non-limiting examples of the function C include the following equations:

$$\min(P_i(v_i) - P_{i+1}(v_{i+1})) \tag{2a}$$

$$|Pi(vi) - Pi+1(vi+1)| \tag{2b}$$

$$\left| \frac{P_i(v_i)}{\mu_i} - \frac{P_{i+1}(v_{i+1})}{\mu_{i+1}} \right| \quad (2c)$$

In the above example for function C, a pixel by pixel comparison of the potential pairs of pixels between the pixels of selected portion 76 of $P_i$ and the pixels of selected portion 78 of $P_{i+1}$ is made to find the minimum difference (2a), the minimum absolute difference (2b) or the minimum absolute difference (2c) of the relative intensity of the pixel to the average value of surrounding pixels. The variable μ represents an average value of pixels in the neighborhood of v. These functions, as well as other criterion functions, which may be recognized by a person of ordinary skill in the art, are used to evaluate each of the possible pairs of locations in projection image $P_i$ and projection image $P_{i+1}$ that can be used to interpolate the value of $X_i$ in the synthetic projection image $P_i$. Each of these possible pairs are evaluated to select the pair of pixel candidates that are most likely the best match for interpolation of the value for pixel $X_i$. It will be recognized that in embodiments wherein the set of projection images includes more than two projection images the criteria functions identified above may be further limited with a comparison to a threshold T, in order to select from a subset of the available voxels.

Next at 310 the value for the pixel $X_i$ is calculated from the selected pixel candidates. This calculation is exemplarily represented with:

$$P(X_i) = G(V_i, V_{i+1}) \quad (3)$$

wherein $P_i$ is the synthetic projection image, $X_i$ is the pixel within the synthetic projection image to be interpolated, and G is a fusion operator applied to the selected values for $V_i$ and $V_{+1}$.

The following equations are examples of fusion operators G which may be used in exemplary embodiments of the method.

$$\max(P_i(v_i), P_{i+1}(v_{i+1})) \quad (4a)$$

$$\min(P_i(v_i), P_{i+1}(v_{i+1})) \quad (4b)$$

$$\frac{P_i(v_i) + P_{i+1}(v_{i+1})}{2} \quad (4c)$$

The exemplary embodiments of the fusion operator G identified above disclose exemplary ways in which the values of the pixels in the selected pair of pixel candidates can be combined to calculate the value of a pixel $X_i$ of the synthetic projection $P_s$. The examples identified above exemplarily take the maximum value between the pixels in the pixel pair (4a), the minimum value of the pixels in the pixel pair (4b), or an average of the two values in the pixel pair (4c). It will be recognized that other functions may be used to determine the value of $X_i$ for the synthetic projection image $P_s$.

At 312 the method is used to create each pixel in the synthetic image $X_{i+n}$. In one embodiment, this may be performed by creating each pixel before incrementing to create a next pixel in the synthetic image while in another embodiment all of the pixels in the synthetic projection image are created in parallel. Persons of ordinary skill in the art will recognize that other processing approaches or orders may be used to create each of the pixels in the synthetic image. This process is repeated until a pixel value $X_{i+n}$ is calculated for each pixel in the synthetic projection image $P_s$, as noted above, it is to be remembered that while the diagrammatic representation of FIG. 5 presents the synthetic projection image $P_s$ as a line, it will be recognized that the acquired projection images and the synthetic projection image are two-dimensional and comprise a plurality of rows of pixels rather than a single row as depicted for conciseness in FIG. 5.

At 314 all pixel values $X_{i+n}$ of the pixels in the synthetic projection image are calculated to create a synthetic projection image at 316. As noted above, embodiments disclosed in further detail herein may include a plurality of synthetic projection images and at 318, after all of the pixels in one synthetic projection image are calculated, the method may be repeated at 318 to calculate a synthetic projection image from a new or additional focal point.

As referenced above, in some embodiments, the set of projection images may include either acquired tomographic projection images, synthetic projection images, or both. In one exemplary embodiment, when a new focal point is received for a synthetic projection image, the selected set of projection images may include the closest available projection images to the received focal point, whether those projection images are acquired tomographic projection images or created synthetic projection images. In an exemplary embodiment, as synthetic projection images are created, those created synthetic projection images may be available and/or used in the creation of further additional synthetic projection images.

Figure 7:
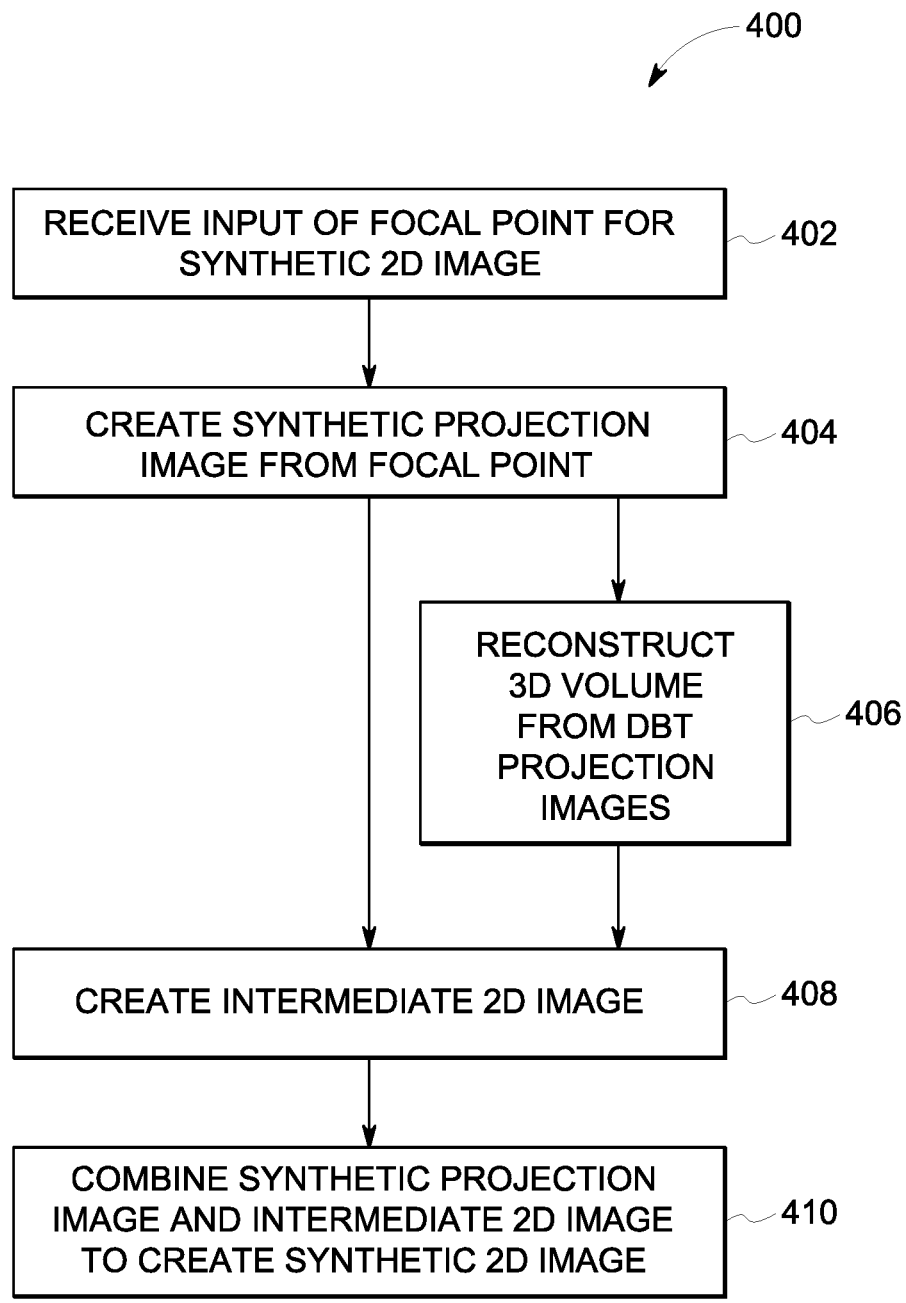
FIG. 7 is a flow chart that depicts an exemplary embodiment of a method of producing a synthetic 2D image from a reconstructed 3D volume.

The created synthetic projection images 316 can be further used to create the synthetic stereo images through exemplary processing as described with respect to method 400 as exemplarily depicted in the flow chart of FIG. 7. At 402 a user input of a focal point for the synthetic 2D image is received. Exemplarily this may be any focal point along the acquisition geometry from the acquisition of the DBT projection images. In other embodiments, this focal point may be independent of acquisition geometry. Exemplarily, the received selected focal point is located between the focal point of two acquired DBT projection images and also is not the same as the focal point at which one of the DBT projection images was acquired.

At 404 a synthetic projection image is created from the user input focal point. Exemplarily, the synthetic projection image is created in accordance with an embodiment of the method 100 described in greater detail above with respect to FIG. 4.

Next, at 406 an intermediate 2D image is created from at least the received focal point for the synthetic projection image. The intermediate 2D image may be created directly from the plurality of projection images.

Optionally, the intermediate 2D image created at 406 may be created from a 3D volume reconstructed from the acquired DBT projection images at 408. In exemplary embodiments, the 3D volume may be a previously acquired medical image volume for example a DBT volume, a CE-DBT volume, an ultrasound volume, or other volumes as may be recognized by a person of ordinary skill in the art. A 3D volume can be reconstructed in a variety of known techniques, including but not limited to a regularized reconstruction technique. In one exemplary embodiment, a filter is applied to the acquired 2D projection images so as to obtain filtered projection images of the object. The filter may be of the high-pass type and have a cutoff frequency which may be determined according to the thickness of the object. Reconstruction slicing of the object are then determined. The reconstruction of the slices may include back-projection of the filtered 2D projection images. This exemplary back-projection may in particular embodiments be of the non linear, "ordered statistics based back-projection" type. In linear back-projection, each voxel of the volume is reconstructed using end pixels of information, each pixel being determined by a projection of the voxel into each of the N projections. In non linear back-projection, the maximum intensity pixel among the N is not used, which makes it possible to considerably reduce the replication artifacts caused by the most intense objects.

It is to be noted that the reconstruction slices of the object of interest represent the reconstruction volume of the object of interest, creating the reconstructed 3D volume, in such an embodiment, the intermediate 2D image is created at 406 from the reconstructed 3D volume. Exemplarily, this is performed by re-projection of the reconstructed 3D volume or reconstructed slices of the 3D volume in the direction of the received input focal point. This re-projection makes it possible to create the intermediate 2D image of the object of interest. At 410 the synthetic projection image is combined with the intermediate 2D image to create a synthetic 2D image from the user selected focal point. This combination may exemplarily be a linear, pixel to pixel combination.

Finally, the synthetic 2D image from the user input focal point may be presented on the graphical display of the imaging system. Additionally, the image processing system may store the synthetic 2D image on the computer memory associated with the image processing unit. The generation of synthetic 2D images similar to those of FFDM 2D images from an arbitrarily selected user input focal point improves clinician review of DBT imaging results by enabling rendering of enhanced quality 2D images from any focal point of the reconstructed 3D volume, rather than limiting the clinician to only those views already represented by the acquired DBT projection images. This may be particularly helpful during clinician review in the event of super position of tissues which may hide lesions or to more accurately determine the location of a lesion or other object of interest in the medical images.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

As used herein an image, for example in phrases including "reconstructing an image," "creating an image," or "producing an image" is not intended to exclude embodiments of the present invention in which data representing an image is generated, but a viewable image is not. However, embodiments may generate (or are configured to generate) at least one viewable image.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of generating images for biopsy control, the method comprising:
   receiving a plurality of tomosynthesis projection images, each tomosynthesis projection image having a respective focal point;
   reconstructing a three-dimensional (3D) volume from the plurality of tomosynthesis projection images;
   producing at least two two-dimensional (2D) synthetic stereo projection images from at least some of the plurality of tomosynthesis projection images, each 2D synthetic stereo projection image having a different focal point from an other 2D synthetic stereo projection image of the at least two 2D synthetic stereo projection images; and
   presenting the at least two 2D synthetic stereo projection images on a graphical display to a clinician for receiving at least one input for biopsy control.

2. The method of claim 1, further comprising mapping pixels of the 2D synthetic stereo projection images to a 3D volume obtained from a prior DBT acquisition, a CE-DBT acquisition, a MRI or an ultrasound acquisition to produce a navigation map for each of the 2D synthetic stereo projection images.

3. The method of claim 2, wherein locations mapped in the navigation map are voxels of the 3D volume obtained from the tomosynthesis projection images.

4. The method of claim 3,
   wherein the navigation map contains height information for each pixel obtained from a synthetic 2D generation process or a reprojection operation of the 3D volume.

5. The method of claim 1, further comprising:
   receiving a user input selecting a point in a 2D synthetic stereo projection image of the at least two 2D synthetic stereo projection images;
   reading the navigation map associated to the 2D synthetic stereo projection image at the user input position;
   identifying a plane through the 3D volume;
   computing a plane location corresponding to the user input position in the identified plane;
   presenting the identified plane on the graphical display with indication of the plane location;
   reprojecting the plane location on another 2D synthetic stereo projection image; and
   displaying the other 2D synthetic stereo projection image with the reprojected location.

6. The method of claim 5 wherein upon receiving a new location to update the position of the location in the identified plane or in the 2D synthetic stereo projection images, the new location is automatically updated in the identified plane and in the 2D synthetic stereo projection images.

7. The method of claim 1, further comprising:
   determining a field of view in each of the plurality of tomosynthesis projection images; and
   producing at least the plurality of 2D synthetic stereo projection images or the 3D volume by discarding areas out of the field of view in at least one of the plurality of tomosynthesis projection images.

8. The method of claim 7, wherein the field of view is at least one of a biopsy window, a paddle area, or an intermediate field of view.

9. The method of claim 1, further comprising:
   identifying an object that projects into the field of view in at least one of the plurality of tomosynthesis projection images; and
   producing at least the plurality of synthetic stereo image or the 3D volume in discarding the identified object area in at least one of the plurality of tomosynthesis projection images.

10. The method of claim 9, further comprising:
    identifying at least one of a coordinate, an orientation, or a trajectory of a biopsy needle in the 3D volume and/or in the synthetic stereo images; and
    presenting on the graphical display at least one of the synthetic stereo images or the 3D volume in combination with at least one of the coordinate, the orientation, and the trajectory of the needle.

11. The method of claim 1 wherein the at least two 2D synthetic stereo projection images are produced by enhancing one baseline projection image using at least a subset of the plurality of tomosynthesis projection images.

12. The method of claim 11 wherein the baseline projection image is obtained from a volume representing the object.

13. The method of claim 11 wherein the baseline projection image is obtained by interpolating a subset of the tomosynthesis projections.

14. The method of claim 11 wherein the baseline projection image is selected from among the plurality of tomosynthesis projection images.

15. The method of claim 14 wherein enhancing the baseline projection image further comprises:
    filtering at least a subset of the tomosynthesis projection images;
    reconstructing a volume from the filtered tomosynthesis projection images;
    reprojecting the volume; and
    combining the volume reprojection with the baseline projection image or a filtered version of the baseline projection image.

16. The method of claim 11 further comprising:
    determining a field of view position in the baseline projection image; and
    enhancing the baseline projection image in an area delimited by the field of view.

17. A system for biopsy control, the system comprising:
    an acquisition unit comprising a radiation source and an X-ray detector, the radiation source movable relative to the X-ray detector to acquire a plurality of projection images at different angulations and each having a respective focal point;
    a graphical display configured to present medical images;
    a control unit communicatively connected to the acquisition unit that operates the acquisition unit to acquire the plurality of projection images and the control unit processes the plurality of projection images to produce a plurality of two-dimensional (2D) synthetic stereo projection images, each 2D synthetic stereo projection image of the plurality having a different focal point from the other 2D synthetic stereo projection images, the control unit communicatively connected to the graphical display to visually present at least one 2D synthetic stereo projection image from the plurality of 2D synthetic stereo projection images on the graphical display; and
    a biopsy robot communicatively connected to the control unit, wherein the control unit receives a user input of a biopsy location based upon the visually presented the at least one 2D synthetic stereo projection image and the control unit operates the biopsy robot to biopsy the biopsy location.

18. The system of claim 17 wherein the acquisition unit comprises a compression paddle with a biopsy window there through and the control unit determines the biopsy window position in each of the plurality of tomosynthesis projection images, extracts image data from within the biopsy window from each of the plurality of tomosynthesis projection images, and produces the plurality of 2D synthetic stereo projection images using the extracted image data of at least one tomosynthesis projection image.

19. The system of claim 17, wherein the control unit further identifies a needle area in the plurality of tomosynthesis projection images and, processes the needle area in each of the plurality of tomosynthesis projection images to attenuate artifacts due to the needle.

20. The system of claim 17, wherein the control unit creates a navigation map mapping the 2D synthetic stereo projection images to the reconstructed 3D volume, and upon receiving at least one user input, navigating between a presentation of a 2D synthetic stereo projection image of the plurality of 2D synthetic stereo projection images on the graphical display to a presentation of at least one 3D tomosynthesis slice of the 3D reconstruction on the graphical display.

21. A method of controlling a needle biopsy, the method comprising:
    receiving a plurality of tomosynthesis projection images, each tomosynthesis projection image having a respective focal point;
    reconstructing a three-dimensional (3D) volume from the plurality of tomosynthesis projection images;
    producing a plurality of two-dimensional (2D) synthetic stereo projection images from the plurality of tomosynthesis projection images, each 2D synthetic stereo projection image of the plurality having a different focal point from the other 2D synthetic stereo projection images;
    presenting the plurality of 2D synthetic stereo projection images on a graphical display to a clinician for receiving at least one input for biopsy control;
    receiving a user input of a location to biopsy in at least one of the 2D synthetic stereo projection images; and
    operating a biopsy robot to move a tip of a biopsy needle to the location.

22. The method of claim 21, further comprising:
    receiving an indication of a biopsy window position;
    determining the biopsy window position in each of the plurality of tomosynthesis projection images;
    extracting image data from within the biopsy window from each of the plurality of tomosynthesis projection images; and
    producing the plurality of 2D synthetic stereo projection images from the extracted image data from each of the plurality of tomosynthesis projection images.

23. The method of claim 21, further comprising:
identifying a needle artifact in the plurality of tomosynthesis projection images; and
before reconstructing the 3D volume and producing the plurality of 2D synthetic stereo projection images, processing the needle artifact in each of the plurality of tomosynthesis projection images to attenuate the needle artifact.

24. The method of claim 21, further comprising mapping the 2D synthetic stereo projection images to the 3D volume, wherein the 3D volume comprises a plurality of 3D tomosynthesis slices to produce a navigation map.

25. The method of claim 24, further comprising:
upon receiving at least one user input, navigating between a 2D synthetic stereo projection image of the plurality of 2D synthetic stereo projection images and at least one 3D tomosynthesis slice of the plurality of 3D tomosynthesis slices based upon the navigation map.

* * * * *